(12) United States Patent
O'Hara et al.

(10) Patent No.: US 12,023,360 B2
(45) Date of Patent: *Jul. 2, 2024

(54) COMPOSITION AND METHODS OF SCREENING

(71) Applicant: OPTIBIOTIX LIMITED, Heslington (GB)

(72) Inventors: Stephen Patrick O'Hara, Heslington (GB); Robert Rastall, Reading (GB)

(73) Assignee: OPTIBIOTIX LIMITED, Heslington (GB)

( * ) Notice: Subject to any disclaimer, the term of this patent is extended or adjusted under 35 U.S.C. 154(b) by 411 days.

This patent is subject to a terminal disclaimer.

(21) Appl. No.: 16/780,572

(22) Filed: Feb. 3, 2020

(65) Prior Publication Data
US 2020/0197452 A1 Jun. 25, 2020

Related U.S. Application Data

(63) Continuation of application No. 15/034,448, filed as application No. PCT/GB2014/053290 on Nov. 5, 2014, now Pat. No. 10,548,927.

(30) Foreign Application Priority Data

Nov. 5, 2013 (GB) ..................... 1319531

(51) Int. Cl.
*A61K 35/747* (2015.01)
*A23L 33/10* (2016.01)
*A23L 33/135* (2016.01)
*A23L 33/21* (2016.01)
*A61K 47/36* (2006.01)
*C12Q 1/04* (2006.01)
*C12Q 1/34* (2006.01)

(52) U.S. Cl.
CPC ............ *A61K 35/747* (2013.01); *A23L 33/10* (2016.08); *A23L 33/135* (2016.08); *A23L 33/21* (2016.08); *A61K 47/36* (2013.01); *C12Q 1/04* (2013.01); *C12Q 1/34* (2013.01); *A23V 2002/00* (2013.01); *G01N 2333/938* (2013.01)

(58) Field of Classification Search
None
See application file for complete search history.

(56) References Cited

PUBLICATIONS

Splechtna, Barbara; et al.; "Production of Prebiotic Galacto-Oligosaccharides from Lactose Using [beta]-Galactosidases from Lactobacillus reuteri" Journal of Agricultural and Food Chemistry, 54, 4999-5006, 2006 (Year: 2006).*

Zheng, Jinshui; et al.; "A taxonomic note on the genus *Lactobacillus*" International Journal of Systematic and Evolutionary Microbiology, 70, 2782-2858, 2020 (Year: 2020).*

(Continued)

*Primary Examiner* — David W Berke-Schlessel
(74) *Attorney, Agent, or Firm* — Nicholas P. Stadnyk; Maynard Nexsen PC

(57) ABSTRACT

The present invention relates to a symbiotic composition comprising a probiotic bacterial strain and a prebiotic growth medium which is specific to the growth of the probiotic bacterial strain, wherein the bacterial strain is capable of producing the same growth medium by reverse enzyme reaction. The present invention also relates to methods of producing and screening for such compositions.

15 Claims, 13 Drawing Sheets

(56) References Cited

PUBLICATIONS

Maischberger et al. βGlactosidase from Lactobacillus pentosus: purification, characterization and formation of galacto-Oligosaccharides, Biotechnology Journal, vol. 5, pp. 838-847, 2010.
Tzortzis, G. et al., Synthesis of α-galactooligosaccharides with α-galactosidase from Lactobacillus reuteri of canine origin, Appl. Microbial Biotechnol, vol. 63, pp. 286-292, published online: Aug. 30, 2003 (Aug. 30, 2003).

* cited by examiner

Sugars

GOS%

Sugars

GOS%

Sugars

GOS%

Sugars

GOS%

Sugars

GOS %

Sugars

GOS%

Sugars

GOS%

COMPOSITION AND METHODS OF SCREENING

CROSS-REFERENCE TO RELATED APPLICATIONS

This application is a continuation of U.S. patent application Ser. No. 15/034,448, filed May 4, 2016, which is a U.S. national stage application under 35 U.S.C. § 371 of International Application No. PCT/GB2014/053290, filed Nov. 5, 2014, which claims priority to Great Britain Application No. 1319531.8, filed Nov. 5, 2013, each of which is incorporated by reference herein in its entirety.

TECHNICAL FIELD OF THE INVENTION

The invention relates to a synbiotic composition comprising a probiotic bacterial strain and a prebiotic growth medium which is specific to the growth of the probiotic bacterial species or strain, wherein the bacterial species or strain is capable of producing the same growth medium by reverse enzyme reaction and methods of identifying and producing such compositions.

BACKGROUND TO THE INVENTION

Probiotics are bacteria which confer health benefits to a host. Typically, cultures of probiotic bacterial strains are consumed or administered to individuals in order to add to and augment the naturally occurring bacteria population of the gut. A number of health benefits have been associated with probiotics, including reducing the incidence of cancer, diarrhoea and irritable bowel syndrome to name a few. Preliminary studies also indicate that probiotics can be useful in reducing serum levels of cholesterol and blood pressure and help modulate diabetes.

Prebiotics are dietary ingredients which can selectively enhance beneficial indigenous gut microbiota, such as lactobacilli or bifidobacteria, and are finding much increased application into the food sector. Prebiotics are non digestible food ingredients that are selectively metabolised by colonic bacteria which contribute to improved health. As such, their use can promote beneficial changes within the indigenous gut microbial milieu and they can therefore help survivability of probiotics. They are distinct from most dietary fibres like pectin, celluloses, xylan, which are not selectively metabolised in the gut. Criteria for classification as a prebiotic is that it must resist gastric acidity, hydrolysis by mammalian enzymes and gastrointestinal absorption, it is fermented by intestinal microflora and selectively stimulates the growth and/or activity of intestinal bacteria associated with health and well-being. There is no known selective prebiotic for Lactobacilli Fructo-oligosaccharides (FOS, inulin and oligofructose) and galactooligosaccharides (GOS) have been demonstrated to fulfil the criteria for prebiotic classification repeatedly in human intervention studies.

Synbiotics are mixtures of probiotics and prebiotics that beneficially affect the host by improving the survival and implantation of probiotics in the gastrointestinal tract, by stimulating the growth and/or by activating the metabolism of one or a limited number of health-promoting bacteria, thus improving host welfare. A product containing oligofructose prebiotic and bifidobacteria probiotic could be considered to be a synbiotic if the mixture benefitted the host. Only a few synbiotics products are currently known.

It is an object of the present invention to provide a synbiotic composition which has a prebiotic component which allows for the specific growth of a given probiotic bacterial species or strain. It is also an object of the present invention to provide for a synbiotic composition which incorporates a Lactobacilli component in which the prebiotic component benefits the growth of lactobacilli species. A yet further object of the present invention is to provide a screening method for identify and matching probiotic bacteria (and strains thereof) and selective prebiotic components so as to form synbiotic compositions which accentuate host benefits.

SUMMARY OF THE INVENTION

In accordance with a first aspect of the present invention, there is provided a synbiotic composition comprising a probiotic bacterial strain and a prebiotic growth medium which is specific to the growth of the probiotic bacterial genus, species or strain, wherein the bacterial strain is capable of producing the same growth medium by reverse enzyme reaction.

By utilising reverse enzyme reaction in the probiotic bacterial strain to produce a prebiotic which is specific to the probiotic and would therefore act as a selective growth medium can be utilised in the synbiotic composition which promotes the growth of the probiotic at the expense of other bacterial strains.

The enzyme may comprise a saccharolytic or glycosidase enzymes. These saccharolytic or glycosidase enzymes may be derived from bacteria or fungi. The prebiotic growth medium may comprise oligosaccharides which may be selected from β-galactosidases, α-galactosidases, α- and β-glucosidases, α-mannosidases, or β-xylosidases.

Preferably, the concentration of the prebiotic growth medium is utilised to determine the probiotic bacterial genus, species or strain.

The bacterial strain preferably comprises a Lactobacilli and may comprises a strain selected from: *Lactobacillus acidophilus, Lactobacillus rhamnosus, Lactobacillus plantarum, Lactobacillusdelbrueckii* ssp. *bulgaricus, Lactobacillus casei, Lactobacillus salivarius, Lactobacillus salivarius* ssp. *salivarius, Lactobacillus fermentum, Lactobacillus reuteri* or *Lactobacillus helveticus*.

The growth medium may comprise oligosaccharides such as galacto-oligosacharides, (GOS), gluco-oligosacharides, or fructo-oligosaccharides (FOS) in varying concentrations. It has been identified in studies that if the growth medium is selective if it comprises 20% or more GOS. Preferably, the composition or growth medium comprises 20% or more GOS. However, the composition or growth medium may comprise a higher amount so that it is more specific for the desired probiotic bacterial genus, species or strain. For example, the composition or growth medium may comprise 25% or more GOS, 30% or more GOS or 40% or more GOS. The composition or growth medium may comprise GOS in the range of 20% to 40%, 20% to 30% or 20% to 25%. It is preferred that the oligosaccharide form is substantially the same as the form produced by β-galactosidases, α-galactosidases, α- and β-glucosidases, α-mannosidases and β-xylosidases reverse reactions of the bacterial strain.

The probiotic bacterial strain will preferably be present in the composition in an effective amount so as to elicit a change in the proportions of the desirable indigenous gut microbiota and in particular the probiotic bacterial strain. Preferably, the probiotic bacterial strain is in an amount in the range of $10^5$ cfu/g to $10^{12}$ cfu/g. More preferably, the probiotic bacterial strain is in an amount in the range of $10^8$ cfu/g to $10^9$ cfu/g. It will be appreciated that the "cfu" refers to colony forming units which is a standard measure of bacterial cell quantity. Furthermore, higher amounts may be utilised if change in the microbiota is required quickly or if the composition is being used to seed the gut with a new bacterial strain not currently present in the body of the human or animal to which the composition in being administered.

The growth medium may be present in an amount which provides optimal growth and survival of the probiotic bacterial strain within the gut without impacting on safety, tolerance, and shelf life.

The strain and/or the growth medium may be encapsulated. Many encapsulation techniques will be apparent to the skilled addressee and the one employed will be tailored to the required stability of the prebiotic growth medium and/or strain and desired digestive transit time. The growth medium may itself be used to encapsulate the strain whether entirely or within an encapsulation matrix formed of the growth medium and another material. It is preferred that the prebiotic growth medium is utilised as an outer core containing the probiotic bacterial strain which is specifically formulated to be released at the target site.

The composition may further comprise an excipient or carrier compound to enable the strain and/or growth medium to pass through the gastrointestinal environment of the body and be efficiently delivered and released to the lower gut. The strain may be concentrated and/or freeze or spray dried. The composition may be in a number of formats, such as a drinkable liquid and/or mixed with a solid or liquid food stuff.

In accordance with a further aspect of the present invention, there is provided a synbiotic composition for the treatment of a metabolic disorder comprising a probiotic bacterial strain and a prebiotic growth medium which is specific to the growth of the probiotic bacterial genus, species or strain, wherein the bacterial strain is capable of producing the same growth medium by reverse enzyme reaction.

The enzyme may comprise a saccharolytic enzyme. The saccharolytic enzyme may be derived from bacteria or fungi. The prebiotic growth medium may comprise oligosaccharides which may be selected from β-galactosidases, α-galactosidases, α- and (3-glucosidases, α-mannosidases, or β-xylosidases.

The bacterial strain preferably comprises a Lactobacilli and may comprises a strain selected from: *Lactobacillus acidophilus, Lactobacillus rhamnosus, Lactobacillus plantarum, Lactobacillusdelbrueckii* ssp. *bulgaricus, Lactobacillus casei, Lactobacillus salivarius, Lactobacillus salivarius* ssp. *salivarius, Lactobacillus fermentum* or *Lactobacillus helveticus.*

The growth medium may comprise oligosaccharides such as galacto-oligosacharides, (Gas), gluco-oligosacharides, or fructo-oligosaccharides (FOS). It is preferred that the oligosaccharide form is substantially the same as the form produced by β-galactosidases, α-galactosidases, α- and β-glucosidases, α-mannosidases and β-xylosidases reverse reactions of the bacterial strain.

The probiotic bacterial strain will preferably be present in the composition in an effective amount so as to elicit a change in the proportions of the desirable indigenous gut microbiota and in particular the probiotic bacterial strain. Preferably, the probiotic bacterial strain is in an amount in the range of $10^5$ cfu/g to $10^{12}$ cfu/g. More preferably, the probiotic bacterial strain is in an amount in the range of $10^8$ cfu/g to $10^9$ cfu/g. Furthermore, higher amounts may be utilised if change in the microbiota is required quickly or if the composition is being used to seed the gut with a new bacterial strain not currently present in the body of the human or animal to which the composition in being administered.

The growth medium may be present in an amount which provides optimal growth and survival of the probiotic bacterial strain within the gut without impacting on safety, tolerance, and shelf life. The concentration of the prebiotic in the medium may be varied to optimise strain, species, and genus specificity.

The strain and/or the growth medium may be encapsulated. Many encapsulation techniques will be apparent to the skilled addressee and the one employed will be tailored to the required stability of the prebiotic growth medium and/or strain and desired digestive transit time. The growth medium may itself be used to encapsulate the strain whether entirely or within an encapsulation matrix formed of the growth medium and another material. It is preferred that the prebiotic growth medium is utilised as an outer core containing the probiotic bacterial strain which is specifically formulated to be released at the target site.

The composition may further comprise an excipient or carrier compound to enable the strain and/or growth medium to pass through the gastrointestinal environment of the body and be efficiently delivered and released to the lower gut. The strain may be concentrated and/or freeze dried. The composition may be in a number of formats, such as a drinkable liquid and/or mixed with a solid or liquid food stuff.

The composition may be formed as a pharmaceutical or medicament which could treat heart disease, diabetes or obesity and other metabolic conditions.

The composition may be administered in up to two or three doses per day. It is preferable that the dosage regime will result in the maintenance of the therapeutically effective amount of prebiotic growth medium and probiotic bacterial strain. The dosage regime may be in conjunction with a foodstuff (including drinks) at pre-determined time points or at meal times.

In accordance with a yet further aspect of the present invention, there is provided synbiotic composition for use as a dietary supplement, nutraceutical or functional food comprising a probiotic bacterial strain and a prebiotic growth medium which is specific to the growth of the probiotic genus, species, or bacterial strain, wherein the bacterial strain is capable of producing the same growth medium by reverse enzyme reaction.

By utilising reverse enzyme reaction in the probiotic bacterial strain to produce a prebiotic which is specific to the probiotic and would therefore act as a selective growth medium can be utilised in the synbiotic composition which promotes the growth of the probiotic at the expense of other bacterial strains.

The enzyme may comprise a saccharolytic enzyme. The saccharolytic enzyme may be derived from bacteria or fungi. The prebiotic growth medium may comprise oligosaccharides which may be selected from β-galactosidases, α-galactosidases, α- and β-glucosidases, α-mannosidases, or β-xylosidases.

The bacterial strain preferably comprises a Lactobacilli and may comprises a strain selected from: *Lactobacillus acidophilus, Lactobacillus rhamnosus, Lactobacillus plantarum, Lactobacillusdelbrueckii* ssp. *bulgaricus, Lacto-* bacillus casei, *Lactobacillus salivarius*, *Lactobacillus salivarius* ssp. *salivarius*, *Lactobacillus fermentum* or *Lactobacillus helveticus*.

The growth medium may comprise oligosaccharides such as galacto-oligosacharides, (GOS), gluco-oligosacharides, or fructo-oligosaccharides (FOS). It is preferred that the oligosaccharide form is substantially the same as the form produced by β-galactosidases, α-galactosidases, α- and β-glucosidases, α-mannosidases and β-xylosidases reverse reactions of the bacterial strain.

The probiotic bacterial strain will preferably be present in the composition in an effective amount so as to elicit a change in the proportions of the desirable indigenous gut microbiota and in particular the probiotic bacterial strain. Preferably, the probiotic bacterial strain is in an amount in the range of $10^5$ cfu/g to $10^{12}$ cfu/g. More preferably, the probiotic bacterial strain is in an amount in the range of $10^8$ cfu/g to $10^9$ cfu/g. Furthermore, higher amounts may be utilised if change in the microbiota is required quickly or if the composition is being used to seed the gut with a new bacterial strain not currently present in the body of the human or animal to which the composition in being administered.

The growth medium may be present in an amount which provides optimal growth and survival of the probiotic bacterial strain within the gut without impacting on safety, tolerance, and shelf life. The concentration of the prebiotic in the medium may be varied to optimise strain, species, and genus specificity The strain and/or the growth medium may be encapsulated. Many encapsulation techniques will be apparent to the skilled addressee and the one employed will be tailored to the required stability of the prebiotic growth medium and/or strain and desired digestive transit time. The growth medium may itself be used to encapsulate the strain whether entirely or within an encapsulation matrix formed of the growth medium and another material. It is preferred that the prebiotic growth medium is utilised as an outer core containing the probiotic bacterial strain which is specifically formulated to be released at the target site.

The composition may further comprise an excipient or carrier compound to enable the strain and/or growth medium to pass through the gastrointestinal environment of the body and be efficiently delivered and released to the lower gut. The strain may be concentrated and/or freeze dried. The composition may be in a number of formats, such as a drinkable liquid and/or mixed with a solid or liquid food stuff.

Furthermore, the composition could be incorporated into an existing food, such as yoghurt or as a powder which can be easily blended with foodstuffs or made into a liquid drink. The composition may be combined with other active ingredients, such as minerals, vitamins and antioxidants.

In accordance with a further aspect of the present invention, there is provided a method of producing a synbiotic composition comprising the steps:
 (a) selecting a probiotic bacterial strain capable of producing a prebiotic growth medium by reverse enzyme reaction; and
 (b) combining the bacterial strain with the growth medium so as to form the composition.

It is preferred that the method is used for producing a composition as herein above described.

In accordance with a yet further aspect of the present invention, there is provided a method for identifying and formulating a synbiotic composition comprising:

(a) a first screening of a number of probiotic bacterial strains for the ability to produce a prebiotic growth medium by reverse enzyme reaction and identifying strains having such ability;
 (b) a second screening of the prebiotic growth mediums of the identified strains for the ability to be a selective growth medium for an individual probiotic bacterial strain; and
 (C) formulating a symbiotic composition comprising the individual probiotic bacterial strain and selective growth medium for that strain.

Preferably, the method is used to form a synbiotic composition as herein above described.

DETAILED DESCRIPTION OF THE INVENTION

Embodiments of the present invention will now be described, by way of example only and with reference to the following Figures:

FIG. 1A-C are graphs show the results of a range of lactobacilli species which were screened for β-galactosidase activity measured at $OD_{420}$ in A MRS broth, B 1% lactose basal media and C 5% lactose basal media;

FIG. 2A 2C are graphs show the results of a range of lactobacilli species which were screened for β-galactosidase activity measured at uM of o-NP in A MRS broth, B 1% lactose basal media and C 5% lactose basal media;

Figure 1A:
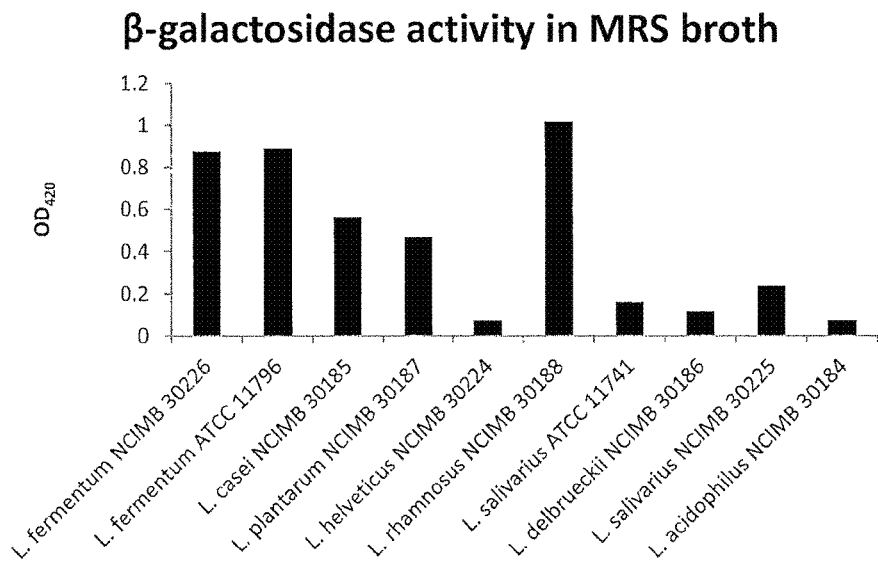

Mechanistically glycosidases are all transferases that use water as their preferred acceptor molecule. Under appropriate circumstance, however, such as high concentrations of substrate carbohydrate, these enzymes will transfer monosaccharide moieties from the substrate (acting as glycosyl donor) to other substrate or non-substrate carbohydrates (acting as glycosyl acceptor). Typically, the products of these reactions are complex mixtures containing all possible glycosidic linkages but in differing amounts. As the reactions are kinetically controlled, the linkage profile synthesised should map onto the rate constants for hydrolysis of those linkages by the producing enzyme. Consequently the oligosaccharides may be more readily metabolised by the producing organisms than by others in the gastrointestinal ecosystem. This approach has shown promise in laboratory testing.

It is possible, however in many enzyme synthesis reactions to include other carbohydrates which will act as acceptors in addition to the lactose. In this way, novel mixtures containing novel structures could be built up.

Probiotic species such as lactobacilli and bifidobacteria are highly saccharolytic and they frequently produce a range of glycosidase enzymes. These enzymes may have transfer activity and be able to synthesise oligosaccharides. This activity is widely reported for β-galactosidases but has not been as intensively studied for other enzymes such as α-galactosidases, α- and β-glucosidases, α-mannosidases, or β-xylosidases. It is also possible to synthesise oligosaccharides using sucrose dependant glycosyltransferases. These transfer either the fructose or glucose moiety from sucrose to sucrose acceptors and build up long polysaccharide chains. In the presence of suitable acceptors, however, they frequently synthesise hetero-oligosaccharides. This has been shown to occur with dextransucrase and alternansucrase and may also occur with laevansucrase.

The experiments sought to explore a strategy to use the products of one synthesis reaction as acceptors in a subsequent reaction. If a probiotic produces a β-galactosidase and a laevan sucrase, for instance, an enzyme extract could be used to synthesise galactooligosaccharides. This product mixture could then be used with the same extract and sucrose as glycosyl donor to bring about the synthesis of fructans many of which would be built up on the galactooligosaccharides which would act as acceptors. In this way novel complex mixtures could be produced that should have a highly tailored fermentation by the producing organism.

One particular experiment was conducted to reversibly use β-galactosidases in microorganisms. Ordinarily, these would digest lactose. However, by changing the reaction conditions, in terms of substrate and temperature, the enzyme acts reversibly and generates an oligosaccharide version of the lactose (GOS).

Lactobacilli are more frequently used as probiotics than are bifidobacteria, yet no prebiotic selective to lactobacilli exists. As these probiotics also harbour β-galactosidase activity, GOS which was specific to these probiotics was produced. The metabolism of prebiotics like GOS are species specific (as evidenced by Bi-Immuno and Bifido bacteria), so a Lactobacilli GOS has the potentially enhance the growth, survivability, and health benefits of lactobacilli. Ultimately, by combining the prebiotic and probiotic an efficacious synbiotic was generated (which would improve gut survival of the former).

The experiments undertaken were as follows:

1. Assemble and test a range of probiotic lactobacilli for their capacity to generate GOS. This would involve measuring β-galactosidase activities;
2. Generate a prebiotic GOS using the reverse enzyme procedure;
3. Scale up of the novel molecule to allow in vitro testing;
4. Compare survival and growth of lactobacilli in the absence and presence of the prebiotic. This would involve a series of 'gut model' experiments that test the probiotics and synbiotics;
5. Research the possibility for using GOS as encapsulation material for the lactobacilli; and
6. Test delivery properties of the encapsulation material.

The GOS prebiotic generated by a specific strain has optimised metabolism not just to produce the GOS, but also to metabolise it (as its generated from a reverse enzyme procedure). The GOS can therefore be incorporated with the probiotic into a synbiotic that would create a highly selective environment for the probiotic. As a probiotic can have a specific health benefits then a synbiotic formula which is tailored to a specific health benefit can be generated.

A screening method for identifying and formulating a synbiotic composition in accordance with an aspect of the invention follows the steps of:
(a) Identifying health need;
(b) Identifying key interjection points for probiotic action e.g BSH activity, cholesterol assimilation & heart disease;
(c) Screening probiotic library using high throughput screening methodology;
(d) Identifying strains with potential activity & health benefits;
(e) Optimising expression of activity using fermentation processes;
(f) Screening strains for glycosidase (e.g beta galactosidase) activity;
(g) Generating a novel oligosaccharide (e.g GOS)
(h) Scaling up to allow in vitro testing;
(i) Comparing survival and growth of the probiotic in the absence and presence of the prebiotic using in vitro plate assays and gut model. If strain characterised then use molecular methodologies to study population changes over time. This will see if affect due to increasing number or increasing activity; and
(j) Combining pre & probiotic to explore Optibiotic affect of combined pre & probiotic.

Evaluation of Anaerobic Utilisation of Novel *L. reuteri* GOS

In these experiments, anaerobic cultures were tested to evaluate the in vitro utilisation of a novel *Lactobacillus reuteri* galactooligosaccharide by monitoring the populations of gut bacterial groups at 24 hours using fluorescent in situ hybridisation, and short-chain fatty acid (SCFA). Fructooligosaccharides (FOS), melibiose and raffinose were used as reference carbohydrates. The table below shows the results of these experiments.

| Group | Inoculum | Melibiose 24 | 24 hr % change | Raffinose 24 | 24 hr % change | FOS 24 | 24 hr % change | GOS 24 | 24 hr % change | GOS + *L. acidophilus* 24 | 24 hr % change | GOS + *L. reuterri* 24 | 24 hr % change |
|---|---|---|---|---|---|---|---|---|---|---|---|---|---|
| Total count | 8.84 | 9.14 | 103% | 9.19 | 104% | 9.2 | 104% | 9.12 | 103% | 9.55 | 108% | 9.34 | 106% |
| Bifidobacteria | 6.85 | 7.33 | 107% | 7.69 | 112% | 7.47 | 109% | 7.69 | 112% | 7.83 | 114% | 8.19 | 120% |
| Bacteroides | 7.98 | 7.9 | 99% | 8.08 | 101% | 8.08 | 101% | 7.95 | 100% | 8.01 | 100% | 7.89 | 99% |
| Lactobacilli | 7.15 | 7.43 | 104% | 7.45 | 104% | 7.32 | 102% | 7.69 | 108% | 7.67 | 107% | 7.73 | 108% |
| Clostridia | 7.55 | 7.65 | 101% | 7.81 | 103% | 8 | 106% | 7.23 | 96% | 7.48 | 99% | 7.2 | 95% |

| | | Melibiose | | Raffinose | | FOS | | GOS | | GOS + L. acidophilus | | GOS + L. reuterri | |
|---|---|---|---|---|---|---|---|---|---|---|---|---|---|
| Group | Inoculum | 24 | 24 hr % change | 24 | 24 hr % change | 24 | 24 hr % change | 24 | 24 hr % change | 24 | 24 hr % change | 24 | 24 hr % change |
| E. coli | 8.14 | 7.66 | *94%* | 8.03 | 99% | 7.85 | *96%* | 8.04 | 99% | 8.24 | 101% | 7.96 | 98% |
| Eubacteria | 8.06 | 7.84 | *97%* | 8.69 | 108% | 8.27 | 103% | *7.75* | *96%* | 8.16 | 101% | 8.28 | 103% |

(Key: BOLD = Significant Increase; Italics = Significant Decrease)

The results show the *Lactobacillus reuterri* GOS showed a significant increase in bifidobacteria and lactobacilli population numbers exhibiting a prebiotic affect. In addition, the GOS increased the growth rate of lactobacilli by 108%, more than any other sugar suggesting a genus specificity. Addition of a strain of *Lactobacillus reuterri* increased the prebiotic affect, increasing the *bifidobacterium* population by 120%.

This suggests that the addition of a GOS producing organism to the GOS produced by that organism had a greater effect on the gut microflora population than the GOS alone.

Lactobacilli β-Galactosidase Screening Assay

Figure 1B:
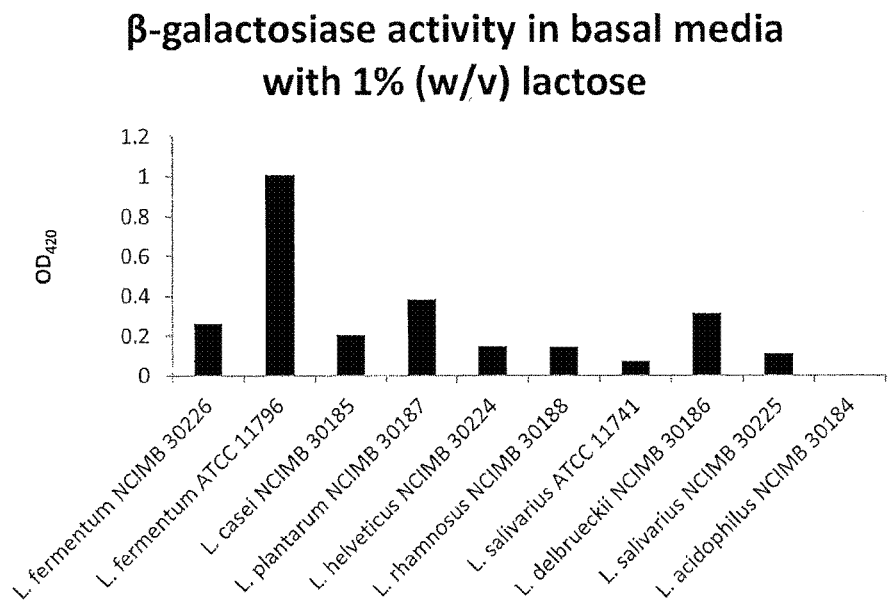
Figure 1C:
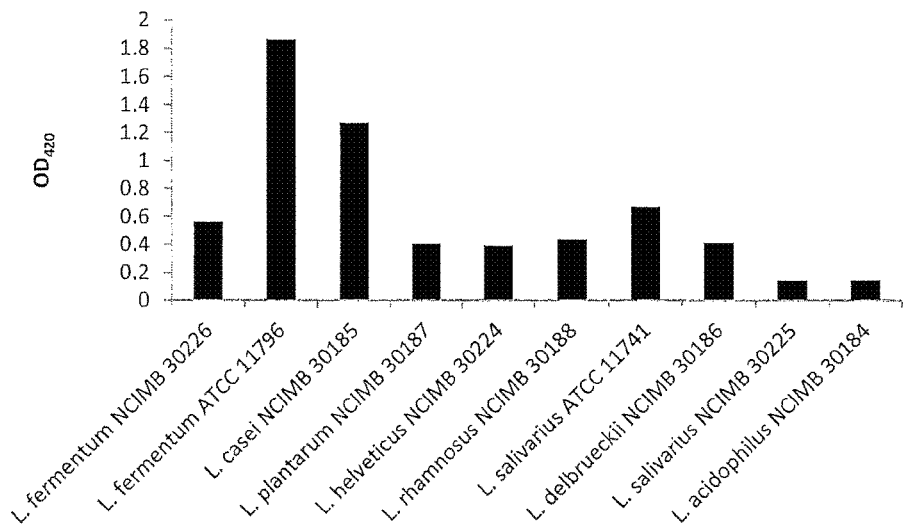
Figure 2A:
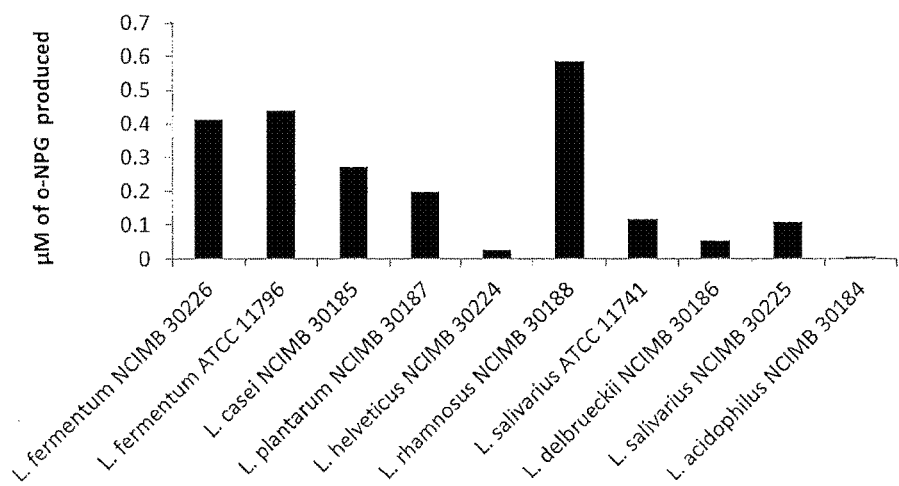
Figure 2B:
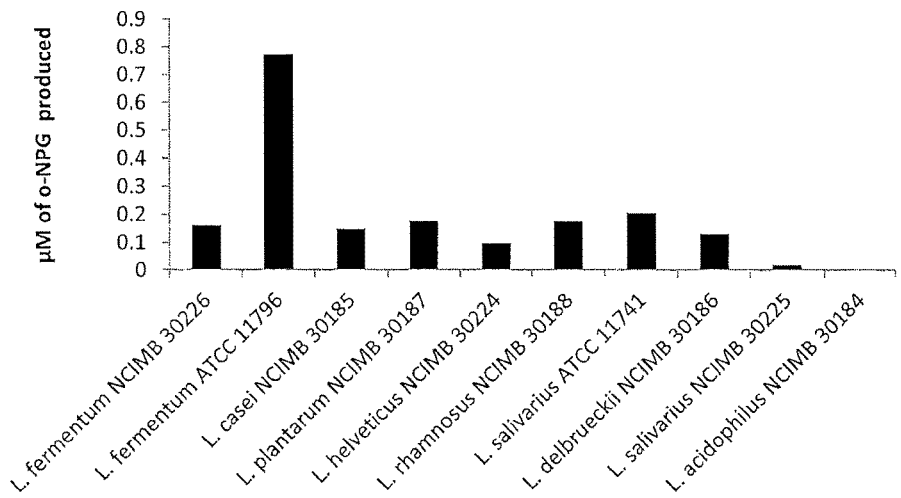
Figure 2C:
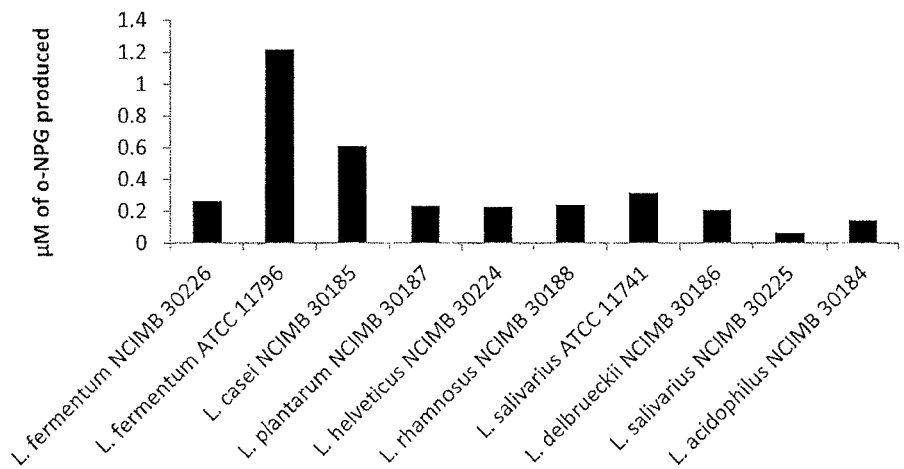

In these experiments, 10 lactobacilli species were screened for β-galactosidase activity in triplicate using standard enzyme assay with o-NPG as substrate. The experiments were carried out in 3 different media; MRS, 1% and 5% lactose in basal media, as lactose is the primary substrate for β-galactosidase it was expected to exhibit highest activity. Activity was measured at time points between time 0-24 hrs, highest activity was shown after 24 hrs. As shown in FIGS. 1-2, in general, 5% lactose exhibits highest enzyme activity and tends to be higher than in MRS broth (contains only glucose as carbon source). High enzyme activity is essential for generating GOS, the 3 organisms which show overall high activity include both *L. fermentum* strains and *L. casei*.

GOS Produced from *L. fermentum* ATCC 11976 and *L. fermentum* NCIMB 30226 in a Long Time Period In these experiments, *L. fermentum* ATCC 11976 and *L. fermentum* NCIMB 30226 were assessed for their production (and consumption) of GOS, lactose and monosaccharides over 168 hours.

Figure 3:
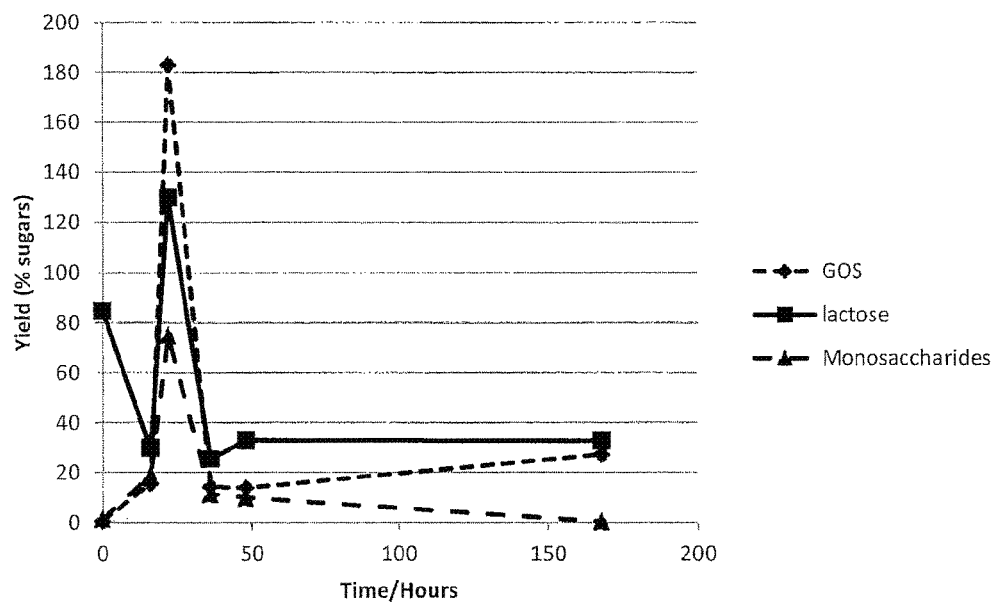
FIG. 3 is a graph showing the yield of GOS, lactose and monosaccharides by *L. fermentum* ATCC 11976 over 168 hours.

The yield of GOS, lactose and monosaccharides for *L. fermentum* ATCC 11976 is shown in the below and in FIG. 3:

| Time point | GOS | lactose | Monosaccharides | Total | GOS % = |
|---|---|---|---|---|---|
| 0 | 0.601 | 85 | 1.464 | 87.065 | 0.690289 |
| 16 | 15.65 | 30.077 | 18.92 | 64.647 | 24.20839 |
| 22 | 183 | 130 | 75 | 388 | 47.16495 |
| 36 | 14.4 | 25.6 | 11.45 | 51.45 | 27.98834 |
| 48 | 14 | 33 | 10 | 57 | 24.5614 |
| 168 | 27.4 | 32.971 | 0.5 | 60.871 | 45.01322 |

Figure 4:
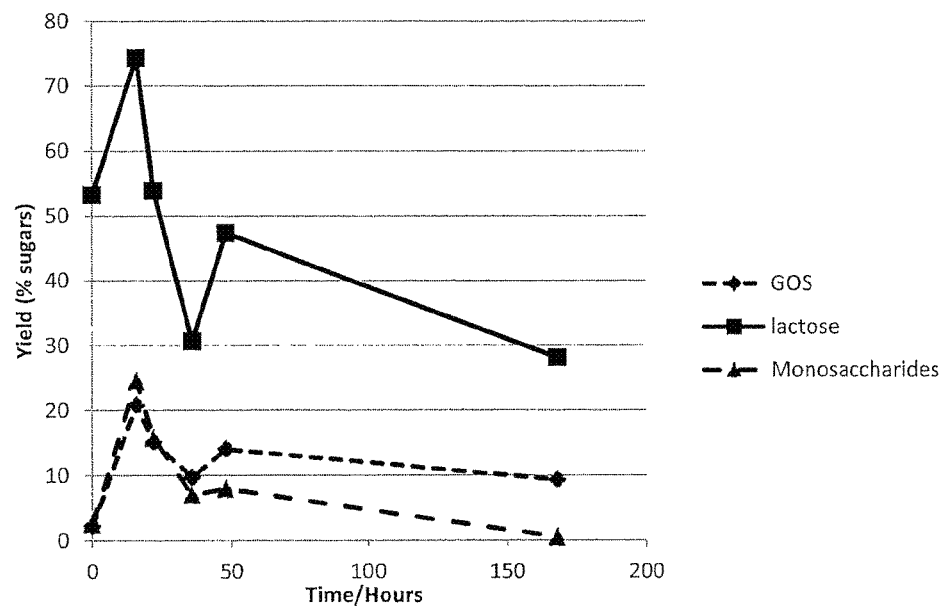
FIG. 4 is a graph showing the yield of GOS, lactose and monosaccharides by *L. fermentum* NCIMB 30226 over 168 hours.
Figure 5:
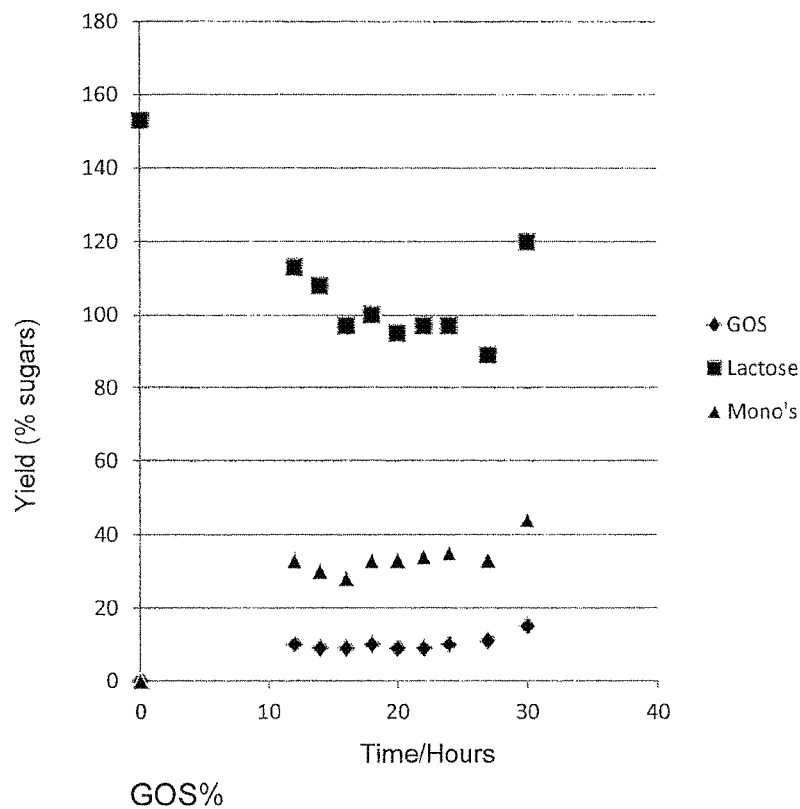
FIGS. 5 & 6 shows graphs of the quantity of Sugars (GOS, Lactose and Monosaccharides) and GOS % over time for *L. fermentum* ATCC 11976.
Figure 5:
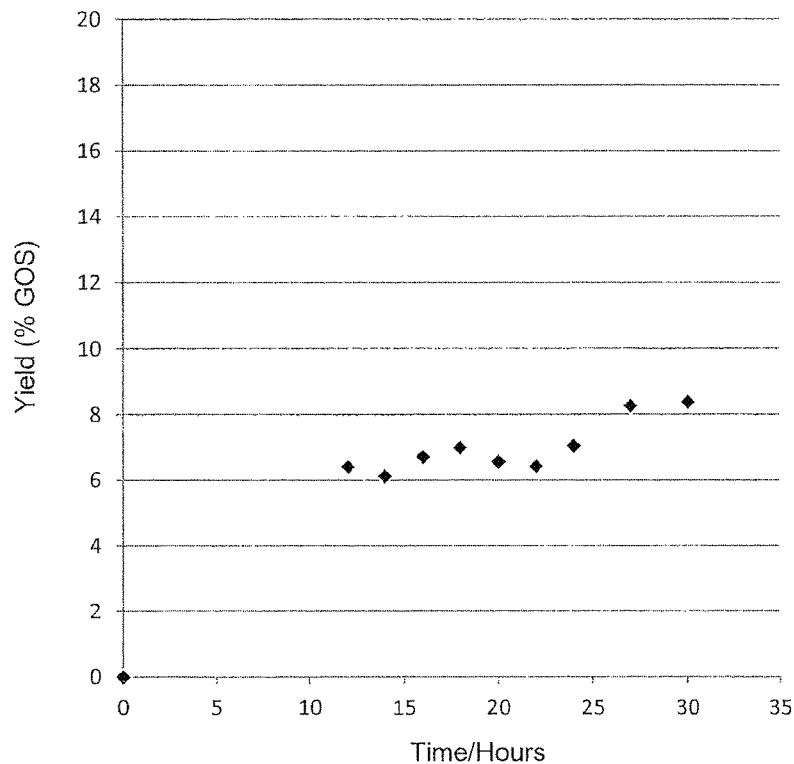
Figure 6:
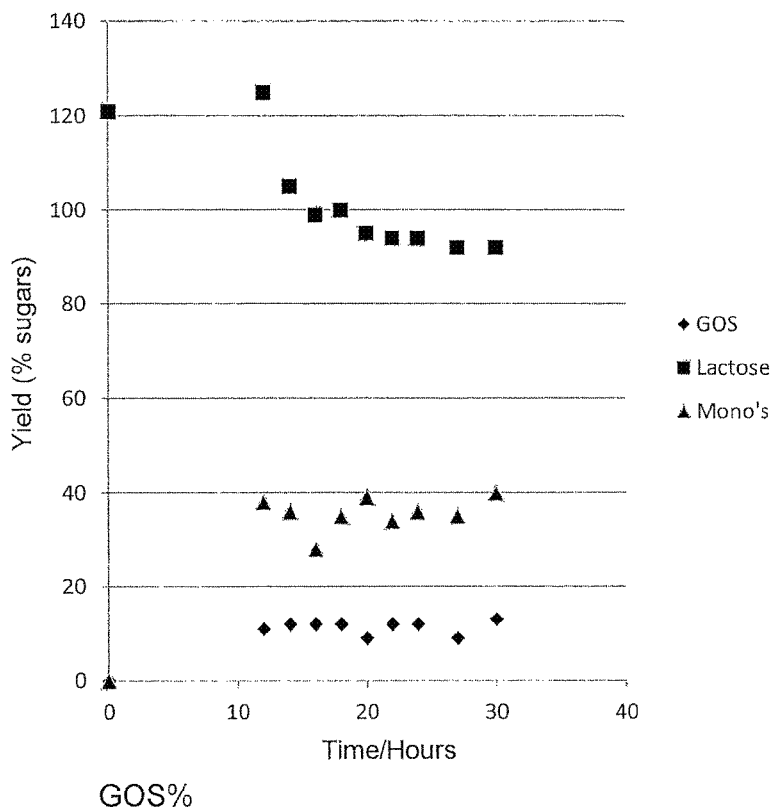
Figure 6:
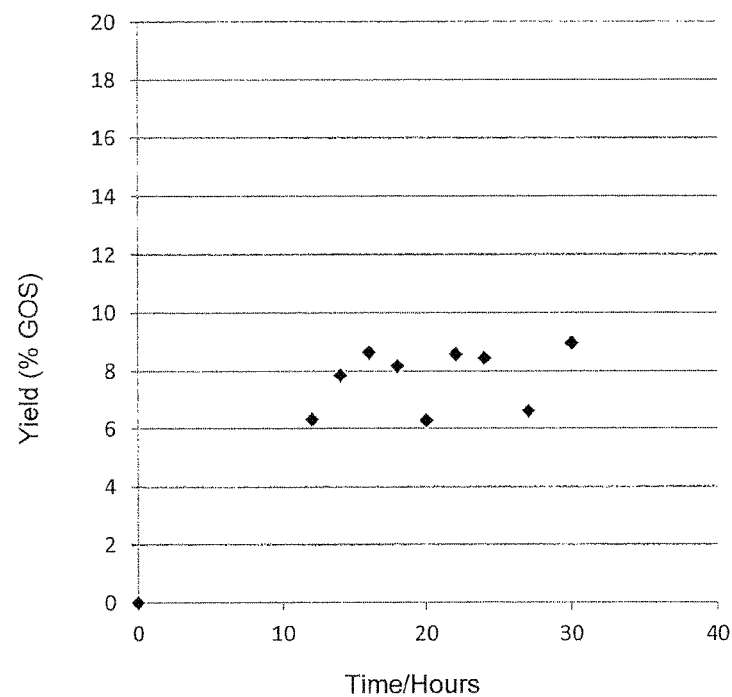
Figure 7:
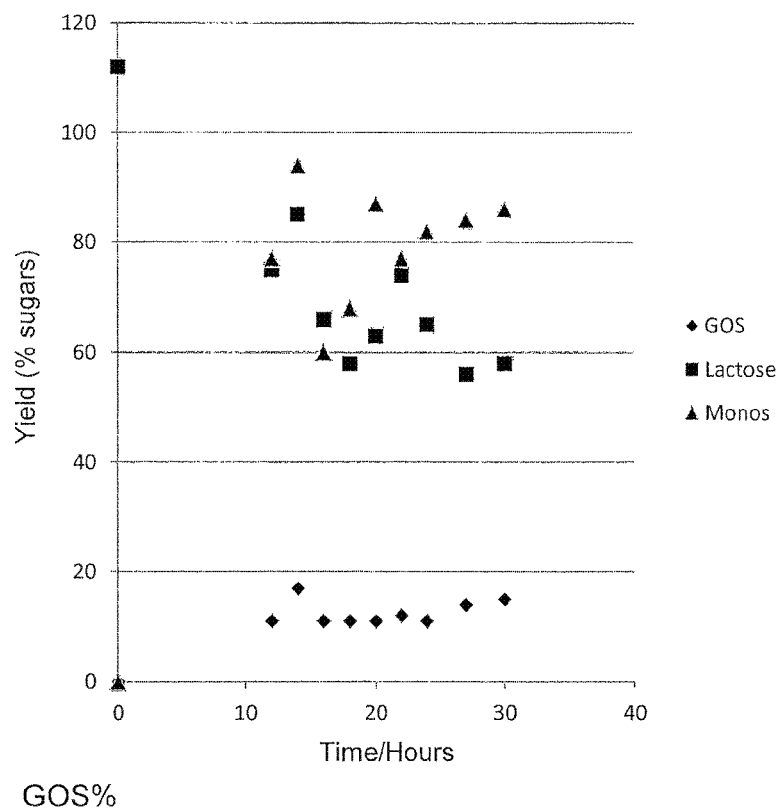
FIGS. 7 & 8 shows graphs of the quantity of Sugars (GOS, Lactose and Monosaccharides) and GOS % over time for *L. fermentum* NCIMB 30226.
Figure 7:
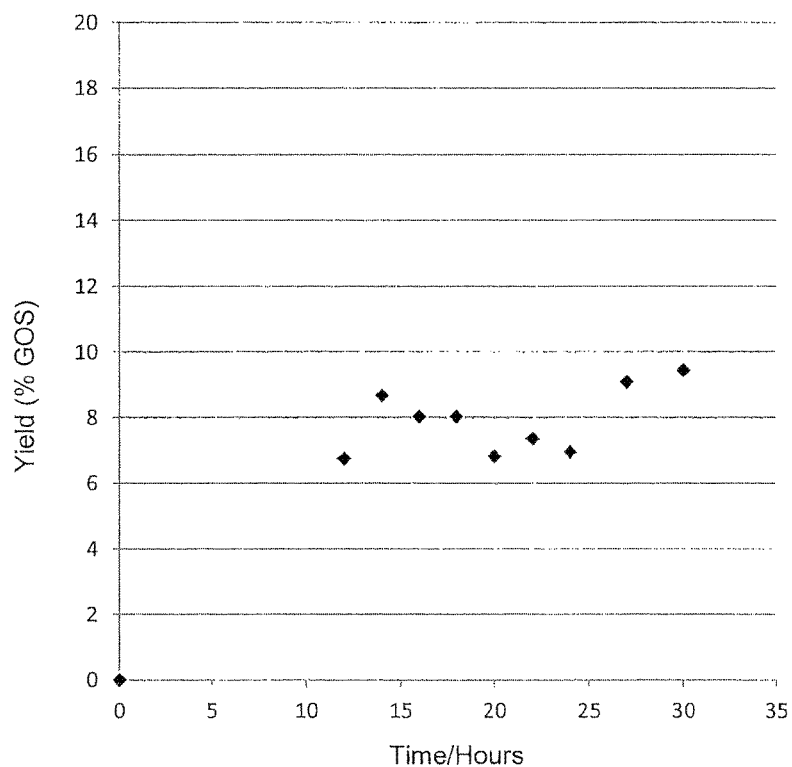
Figure 8:
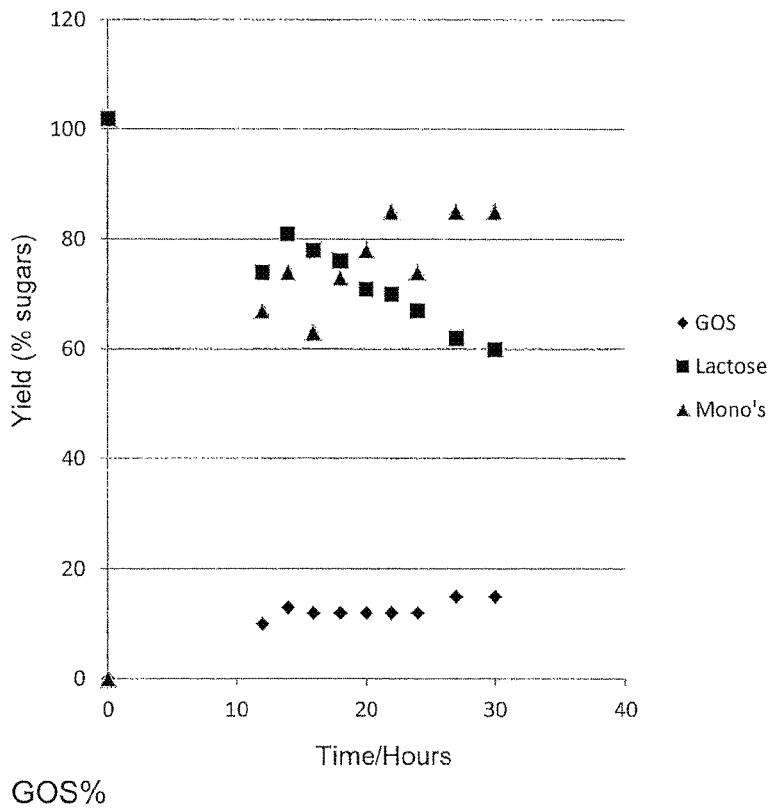
Figure 8:
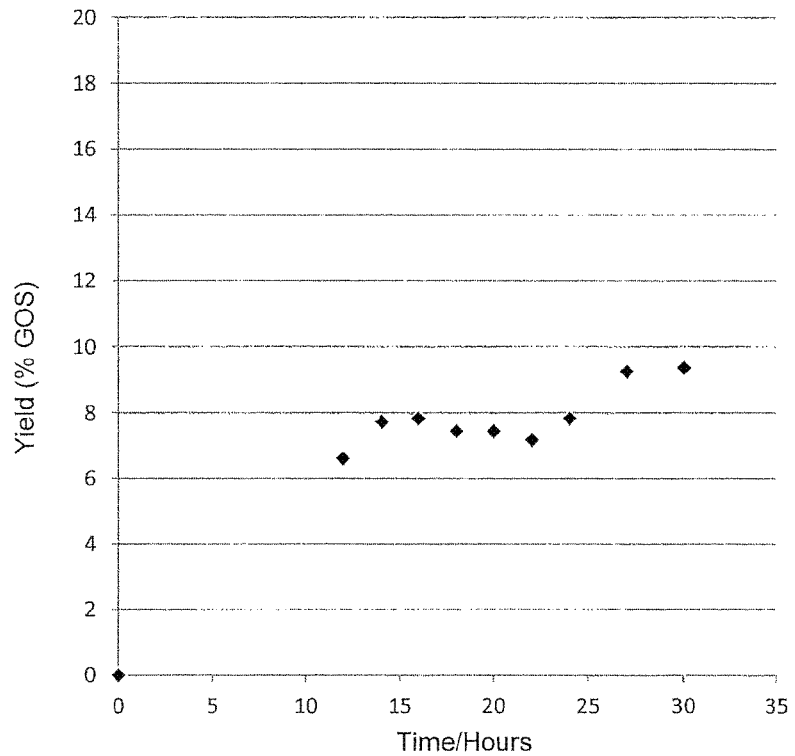
Figure 9:
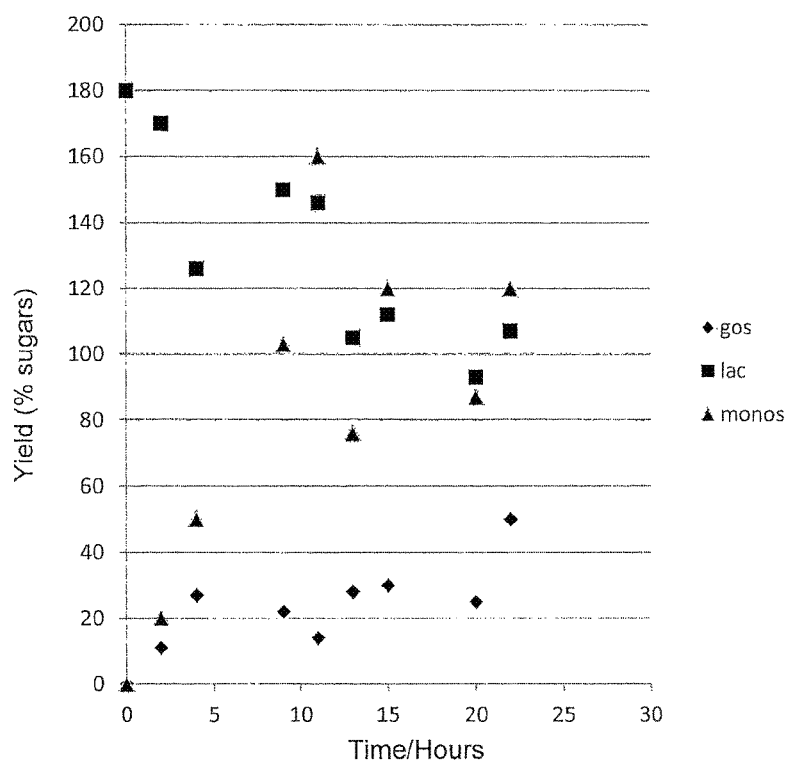
FIG. 9 shows graphs of the quantity of Sugars (GOS, Lactose and Monosaccharides) and GOS % over time for 18U. *L. fermentum* ATCC 11976.
Figure 9:
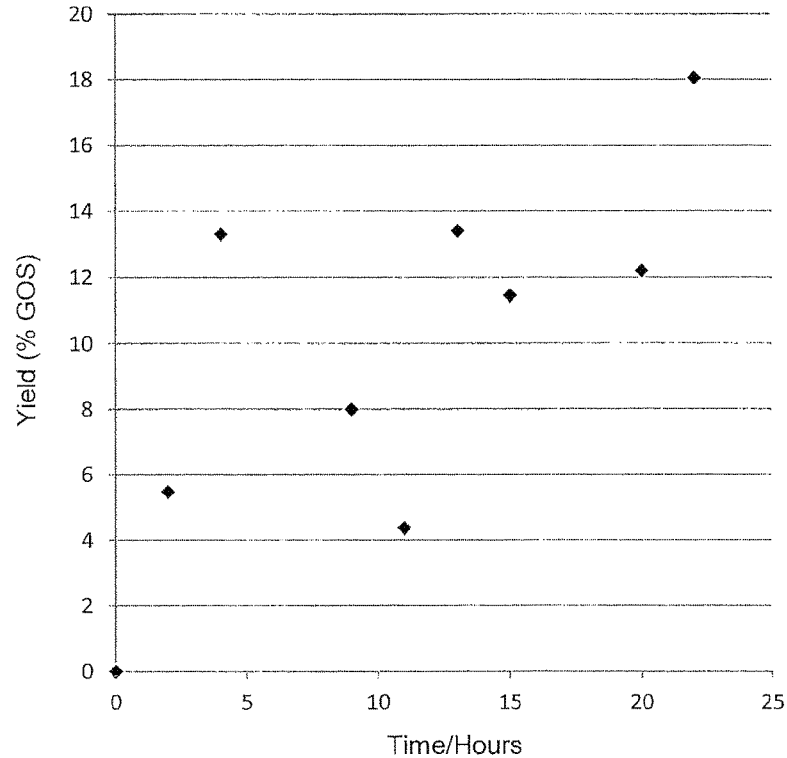
Figure 10:
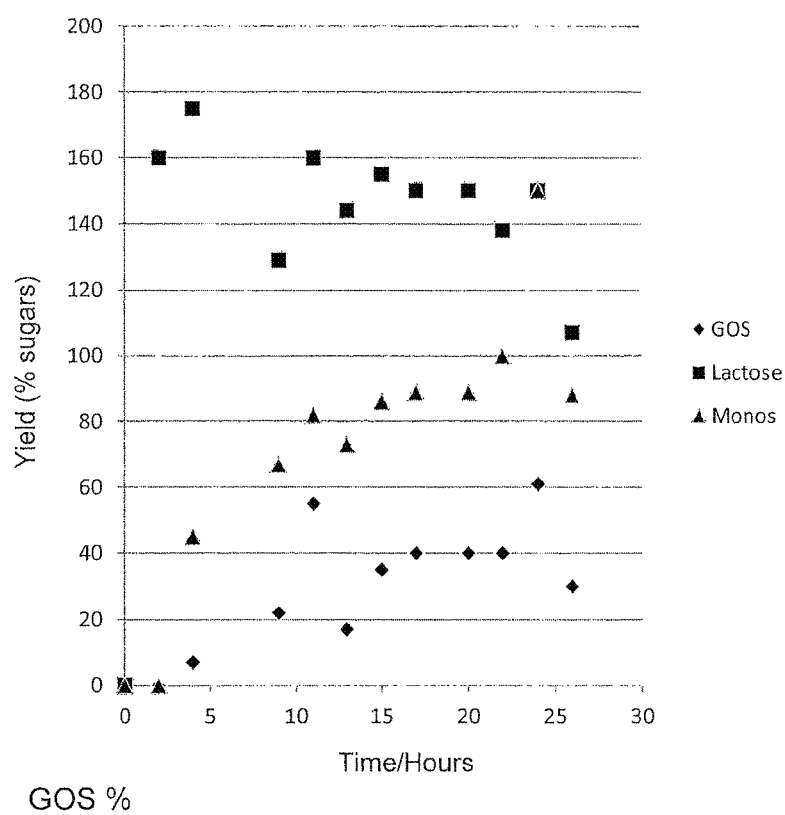
FIG. 10 shows graphs of the quantity of Sugars (GOS, Lactose and Monosaccharides) and GOS % over time for 18U. *L. fermentum* NCIMB 30226.
Figure 10:
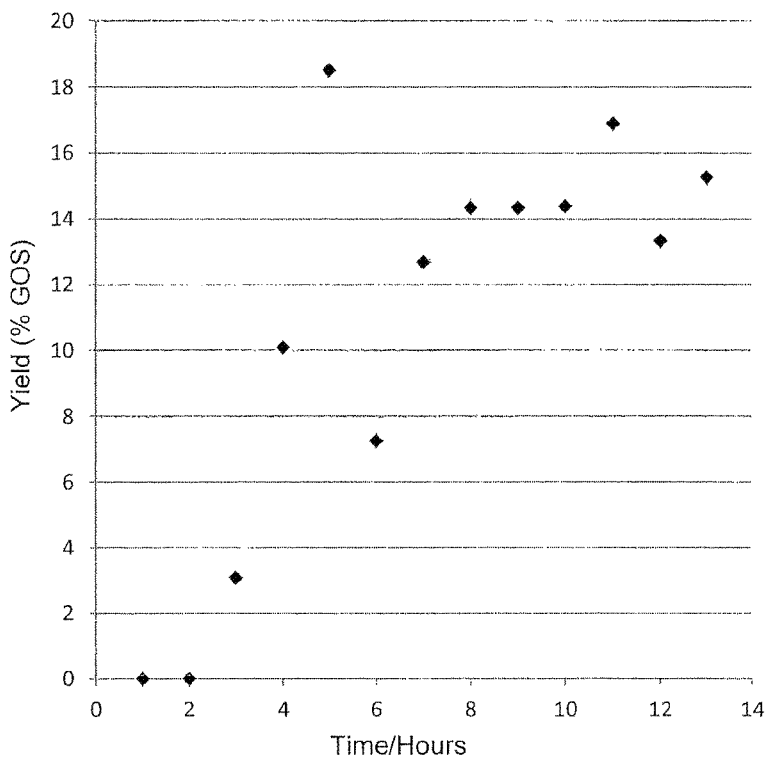
Figure 11:
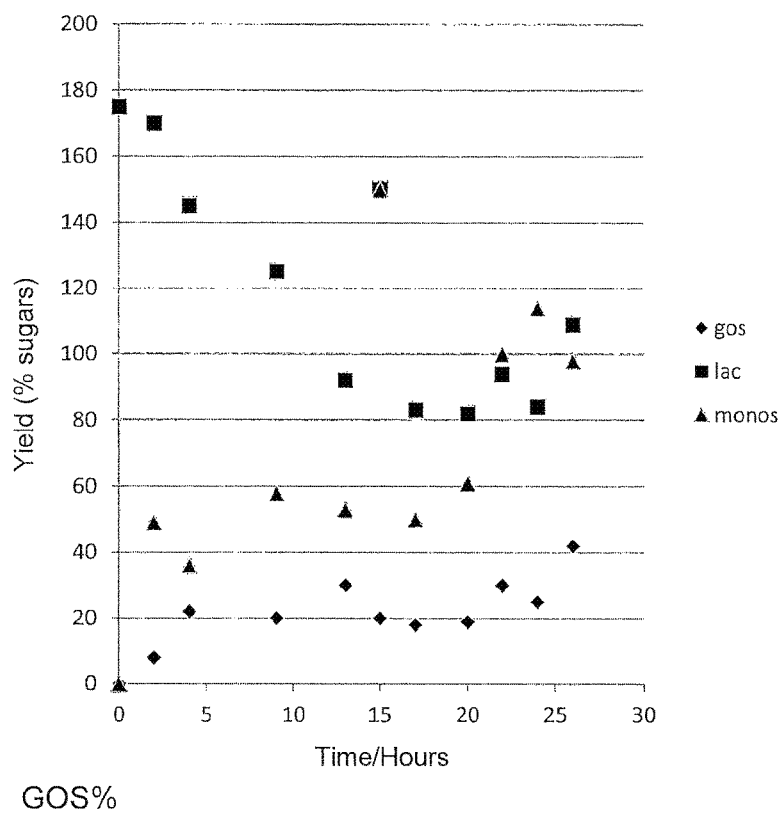
FIG. 11 shows graphs of the quantity of Sugars (GOS, Lactose and Monosaccharides) and GOS % over time for 30U. *L. fermentum* ATCC 11976.
Figure 11:
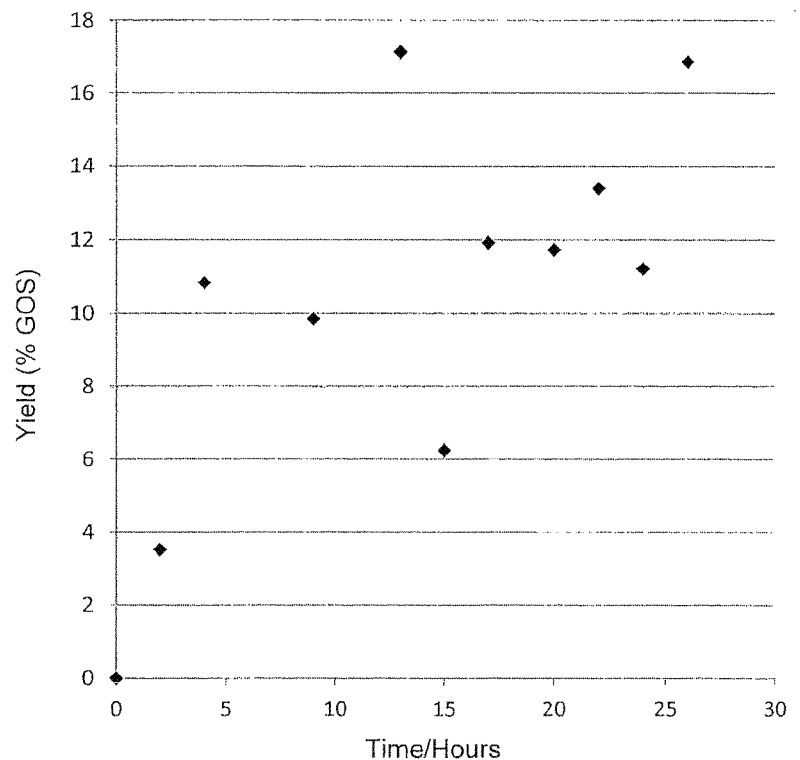
Figure 12:
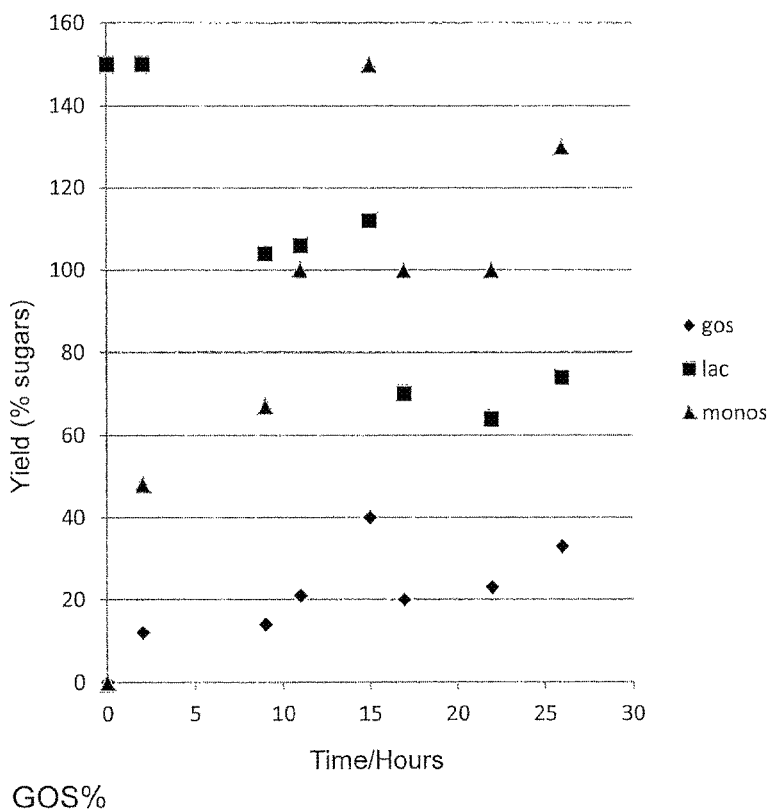
FIG. 12 shows graphs of the quantity of Sugars (GOS, Lactose and Monosaccharides) and GOS % over time for 30U. *L. fermentum* NCIMB 30226.
Figure 12:
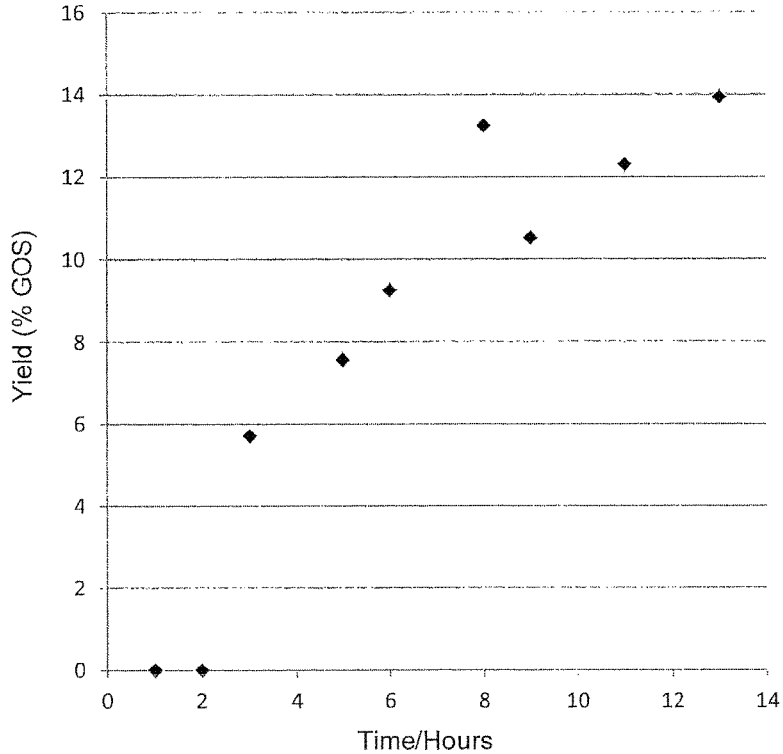

The yield of GOS, lactose and monosaccharides for *L. fermentum* NCIMB 30226 is shown in the below and in FIG. 4:

| Time point | GOS | lactose | Monosaccharides | Total | GOS % = |
|---|---|---|---|---|---|
| 0 | 2.206 | 53.309 | 2.538 | 58.053 | 3.799976 |
| 16 | 20.789 | 74.275 | 24.481 | 119.545 | 17.3901 |
| 22 | 15.066 | 53.918 | 15.713 | 84.697 | 17.78812 |
| 36 | 9.699 | 30.672 | 6.977 | 47.348 | 20.4845 |
| 48 | 13.971 | 47.341 | 7.944 | 69.256 | 20.17298 |
| 168 | 9.3 | 28.125 | 0.521 | 37.946 | 24.50851 |

GOS Produced from *L. fermentum* ATCC 11976 in a 20% Lactose Medium Over 24 Hours In this experiment, GOS synthesis from *L. fermentum* ATCC 11976 β-galactosidase was investigated. After lysis, the crude extract was incubated in 20% lactose over 24 hr and samples taken at time 0 and 24.

The table below shows the sugars present at T0:

| No. | Ret. Time min | Height v | Width min | Type | Asym. (EP) | Plates (EP) |
|---|---|---|---|---|---|---|
| 1 | 0.226 | 0.397 | n.a. | BM | n.a. | n.a. |
| 2 | 0.689 | 0.283 | n.a. | MB | n.a. | n.a. |
| 3 | 6.912 | 1.743 | n.a. | Ru | n.a. | n.a. |
| 4 | 8.436 | 1.465 | n.a. | Ru | n.a. | n.a. |
| 5 | 9.072 | 1.234 | n.a. | Ru | n.a. | n.a. |
| 6 | 10.716 | 13.758 | 1.419 | BMb | 0.87 | 851 |
| 7 | 14.403 | 0.605 | n.a. | Ru | n.a. | n.a. |
| 8 | 18.457 | 16.603 | n.a. | bM | n.a. | n.a. |
| 9 | 18.694 | 17.001 | n.a. | M | n.a. | n.a. |
| 10 | 22.318 | 0.373 | n.a. | Ru | n.a. | n.a. |
| 11 | 24.168 | 29.345 | 29.609 | M | n.a. | n.a. |
| 12 | 28.157 | 150.287 | 1.544 | MB | n.a. | 5436 Lactose |
| n.a. | n.a. | n.a. | n.a. | n.a. | n.a. | n.a. |
| Average: | | 19.424 | 10.857 | | 0.87 | 3144 |

The table below shows the sugars present at T24:

| Ret. Time min | Height v | Width min | Type | Resol. (EP) | Asym. (EP) | Plates (EP) |
|---|---|---|---|---|---|---|
| 2.506 | 0.010 | n.a. | BMB | n.a. | 1.52 | 128 |
| 6.903 | 0.097 | n.a. | BM | n.a. | n.a. | n.a. |
| 10.624 | 10.367 | 1.121 | M | 1.75 | n.a. | 1425 |
| 15.062 | 3.082 | 3.812 | MB | 2.17 | n.a. | 232 |

-continued

| Ret. Time min | Height v | Width min | Type | Resol. (EP) | Asym. (EP) | Plates (EP) | |
|---|---|---|---|---|---|---|---|
| 20.868 | 1.220 | 1.268 | BMB | 2.66 | 0.65 | 3522 | |
| 24.177 | 10.614 | 1.097 | BMb | 3.50 | 1.57 | 7869 | GOS |
| 28.167 | 73.205 | 1.207 | bM | n.a. | 1.45 | 8860 | Lactose |
| 29.600 | 5.009 | 2.231 | M | n.a. | n.a. | n.a. | |
| 32.806 | 10.232 | 1.873 | M | 1.05 | n.a. | 5038 | Glucose |
| 34.822 | 8.609 | 2.038 | M | n.a. | n.a. | 4812 | Galactose |
| 41.161 | 0.867 | n.a. | M | n.a. | n.a. | n.a. | |
| 43.560 | 0.590 | n.a. | M | n.a. | n.a. | n.a. | |
| 46.616 | 0.386 | n.a. | M | n.a. | n.a. | n.a. | |
| 49.693 | 0.107 | n.a. | MB | n.a. | n.a. | n.a. | |
| 51.010 | 0.006 | n.a. | bMB | n.a. | n.a. | n.a. | |
| 54.025 | 0.006 | n.a. | BMB | 1.18 | 1.41 | 774387 | |
| 54.751 | 0.008 | n.a. | BMB | n.a. | 1.27 | 48500 | |
| n.a. | n.a. | n.a. | n.a. | n.a. | n.a. | n.a. | |
| | 7.319 | 1.831 | | 2.05 | 1.31 | 85477 | |

GOS Produced from *L. fermentum* ATCC 11976 and *L. fermentum* NCIMB 30226 in a Short Time Period In this experiment, GOS was produced from *L. fermentum* ATCC 11976 and *L. fermentum* NCIMB 30226 and the enzyme activity of the sugars vs the % GOS assessed over 50 hours as this was when most activity took place during the previous experiments.

Protocol

GOS was produced using the following protocol:
1. Set up 50 ml overnight cultures in modified MRS broth supplemented with 2% lactose for *L. fermentum* ATCC 11976 and *L. fermentum* NCIMB 30226;
2. Suspend 50 ml of overnight culture in 1 L of mMRS broth with 2% lactose;
3. Incubate in anaerobic cabinet at 37° C.;
4. *L. fermentum* ATCC 11976 for 14 hours;
5. *L. fermentum* NCIMB 30226 for 8 hours;
6. Measure $OD_{660}$;
7. Centrifuge cultures, 10 000 g×10 mins;
8. Make up 40% lactose in sodium phosphate buffer. 400 g/L;
9. Pour off supernatant;
10. Resuspend pellets in sodium phosphate buffer (50 mM, pH 6.8);
11. Pool pellets in 50 ml falcons;
12. Freeze thaw in Liquid Nitrogen ×3;
13. French Press, 30,000 PSI, 1 pass, 5 drops/min;
14. Spin down lysate—15,000 g×45 min;
15. Pour supernatant into fresh falcon;
16. Carry out β gal activity assay to work enzyme concentrations;
17. Incubate the free cell extract with 40% lactose/sodium phosphate buffer;
18. Sample 200 μl every 2 hours over 50 hours;
19. Freeze samples;
20. Filter sterilise all samples through 0.2 μm filter;
21. Analyse on HPLC.

Results—GOS Production

As shown in FIGS. 5 to 8, there was a 30-45% lactose conversion and 10% GOS yield.

Enzyme Activity

A further experiment was conducted in order to ascertain the enzyme activity (and therefore efficiency) of the GOS produced from *L. fermentum* ATCC 11976 and *L. fermentum* NCIMB 30226.

Cultures were grown for 8 hrs F, 14 hr for F* in 1 L and harvested at 12,000 g×10 min. The cells were lysed and cell extract spun down 15,000 g×45 min. This was then incubated at 40° C. in 40% lactose sodium phosphate buffer +$MgCl_2$ with same U of enzyme/reaction and activity analysed on an HPLC at 2 hour time points for 36 hours.

The enzyme unit calculations were as follows:

| Organism | OD pre harvest | $OD_{420}$ (enzyme) after french press | $OD_{420}$ (enzyme) after final spin | Enzyme U/15 ml |
|---|---|---|---|---|
| F*1 | 0.83 | 2.4605 | 2.3315 | 18.23977 |
| F*2 | 0.86 | 1.83 | 3.1955 | 30.17002 |
| F1 | 0.94 | 1.833 | 3.812 | 30.0665 |
| F2 | 1.13 | 1.5739 | 6.0115 | 47.63684 |

Where F*1, F2 18U/reaction, F*2, F1 30U/reaction.

Results

As shown in FIGS. 9 to 12, there was a 40-50% lactose conversion and 15-20% GOS yield.

Lactobacilli Specificity with GOS Purity

In this experiment, GOS produced from *L. fermentum* ATCC 11976 used as part of the growth media for a range of bacteria to see if this species specific GOS provided any growth specificity.

GOS Synthesis

*L. fermentum* ATCC 11976 was grown in modified MRS supplemented with 2% lactose in 1 L cultures for 14 hours. The culture was spun down and resuspend in a sodium phosphate buffer. The cells were lysed using liquid Nitrogen and a French Press and the lysate spun to obtain free cell extract. The free cell extract was incubated with 40% Lactose and a sample taken every 2 hours over 50 hours. Samples were loaded on HPLC after every time point for analysis.

Growth Curves 20% GOS Mixture

1% of the impure GOS produced earlier was added to 9 ml mMRS hungates. The growth of a range of organisms were on this mixture were analysed: *Clostridium difficile, Bifidobacterium bifidum, Bifidobacterium longum, Lactobacillus fermentum* ATCC 11976, *Lactobacillus fermentum, Lactobacillus rhamnosus, Lactobacillus casei* & *Lactobacillus delbrueccki*. Experiments were conducted in 3 repeats in triplicate with enumeration at 0, 3, 6, 8, 16 and 24 hours.

Results

Figure 13:
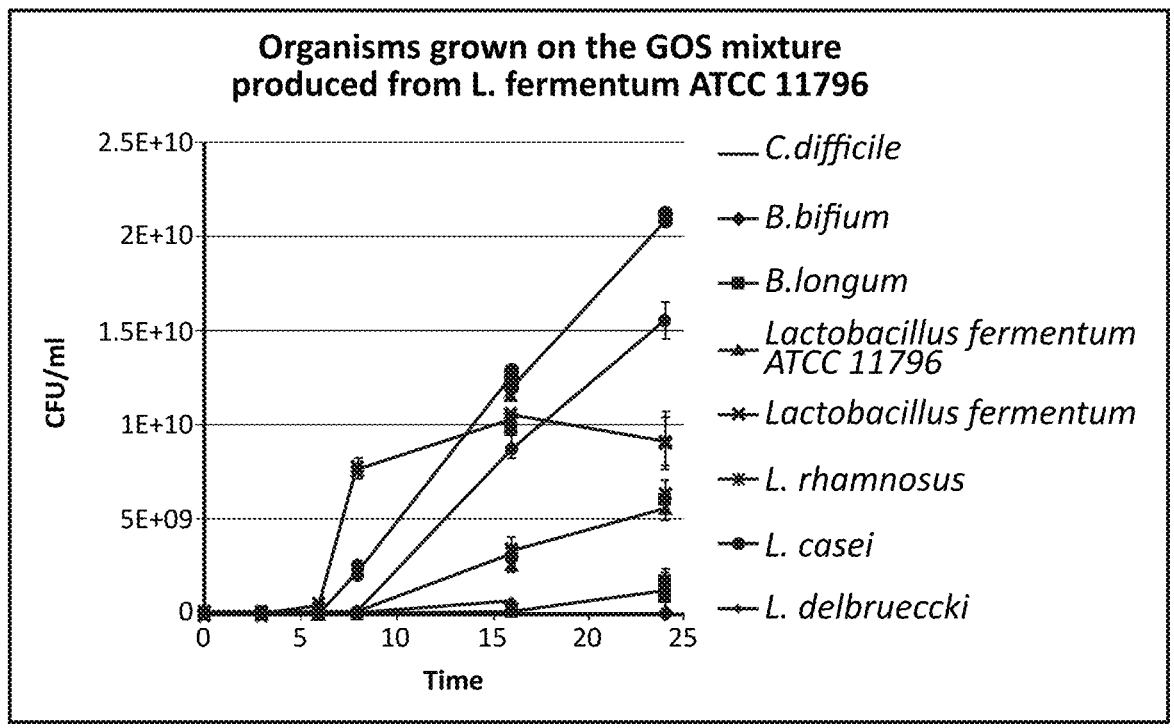
FIG. 13 is a graph illustrating the relative growth profiles of a range of bacteria grown on a GOS mixture produced from *L. fermentum* ATCC 11976.
Figure 14:
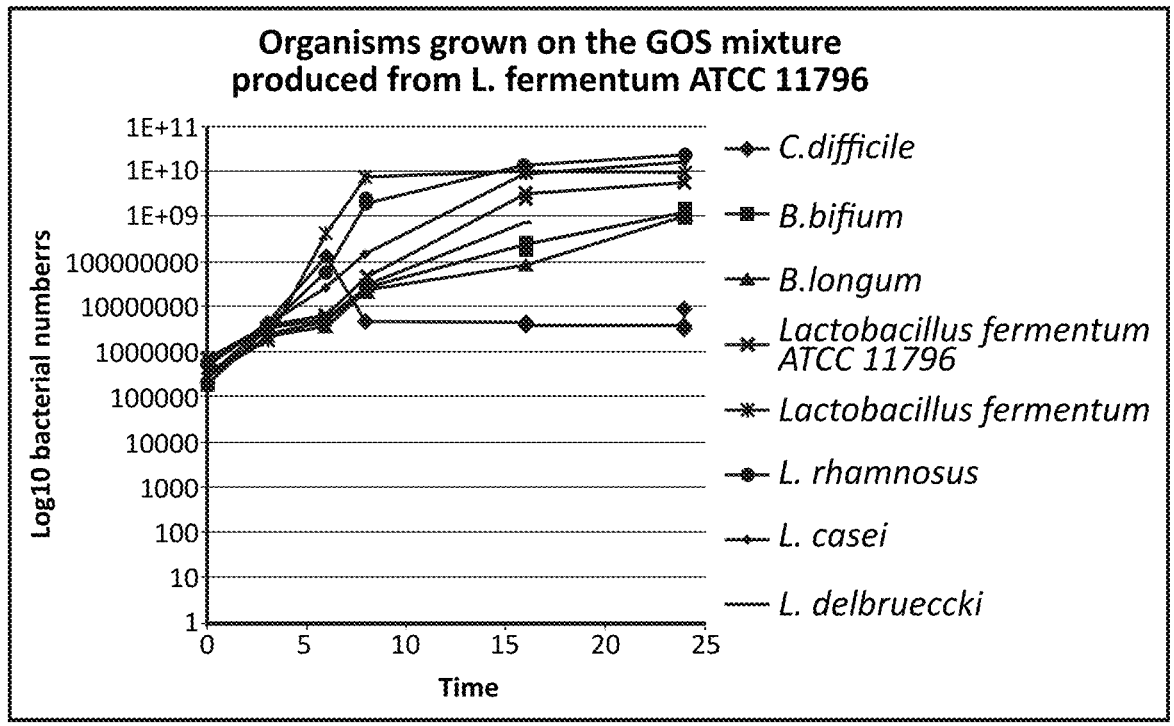
FIG. 14 is a second graph illustrating the relative growth profiles of a smaller range of bacteria grown on a GOS mixture produced from *L. fermentum* ATCC 11976.

As shown in FIGS. 13 and 14, little growth was found in *C. difficile*, whereas the best growth was found in *L. rhamnosus*. The 20% GOS mixture was generally more selective towards lactobacilli.

The forgoing embodiments are not intended to limit the scope of the protection afforded by the claims, but rather to describe examples of how the invention may be put into practice.

The invention claimed is:

1. A synbiotic composition comprising:
a Lactobacilli probiotic strain comprising a β-galactosidase enzyme producing a β1-4 linked galacto-oligosaccharide (GOS) through a reverse (3-galactosidase enzyme reaction; and
a prebiotic growth medium comprising β1-4 linked GOS produced by the Lactobacilli probiotic strain through the reverse β-galactosidase enzyme reaction, wherein the Lactobacilli probiotic strain comprises a strain selected from *Lactobacillus fermentum* ATCC 11976 or *Lactobacillus fermentum* NCIMB 30226.

2. The composition of claim 1, wherein the concentration of the prebiotic growth medium is determined by the probiotic strain.

3. The composition of claim 1, wherein the Lactobacilli probiotic strain is in an amount in the range of $10^5$ cfu/g to $10^{12}$ cfu/g.

4. The composition of claim 1, wherein the Lactobacilli probiotic strain and/or the growth medium is encapsulated.

5. The composition of claim 4, wherein the growth medium encapsulates the Lactobacilli probiotic strain.

6. The composition of claim 1, wherein the composition further comprises an excipient or carrier compound that enables the Lactobacilli probiotic strain and/or growth medium to pass through the gastrointestinal environment of the body.

7. The composition of claim 1, wherein the Lactobacilli probiotic strain is concentrated and/or freeze dried.

8. The composition of claim 1, wherein the composition is in the form of a drinkable liquid and/or can be mixed with a solid or liquid food stuff.

9. The composition of claim 1, wherein the growth medium comprises 20% or more of the β1-4 linked GOS produced by the Lactobacilli probiotic strain.

10. A medicament comprising the composition of claim 1, wherein the medicament comprises the Lactobacilli probiotic strain in an amount in the range of $10^8$ cfu/g to $10^9$ cfu/g.

11. A dietary supplement comprising the composition of claim 1, wherein the growth medium comprises 20% or more GOS.

12. A method of producing a synbiotic composition comprising:
selecting a Lactobacilli probiotic strain comprising a β-galactosidase enzyme producing a β1-4 linked galacto-oligosaccharide (GOS) through a reverse β-galactosidase enzyme reaction, the Lactobacilli probiotic strain producing a prebiotic growth medium comprising the β1-4 linked GOS;
establishing a concentration of the pre biotic growth medium to provide growth selectivity of the desired quantity of the pro biotic bacterial strain; and
combining the bacterial strain with the established concentration of growth medium to form the synbiotic composition, wherein the Lactobacilli probiotic strain comprises a strain selected from *Lactobacillus fermentum* ATCC 11976 or *Lactobacillus fermentum* NCIMB 30226.

13. The method of claim 12, further comprising producing the prebiotic growth medium with the Lactobacilli probiotic strain.

14. The method of claim 13, wherein the growth medium comprises 20% or more of the β1-4 linked GOS produced by the Lactobacilli probiotic strain.

15. The method of claim 12, further comprising encapsulating the synbiotic composition.

* * * * *